United States Patent [19]
Goor et al.

[11] Patent Number: 5,178,137
[45] Date of Patent: Jan. 12, 1993

[54] SEGMENTED DYNAMIC SPLINT

[75] Inventors: Dan Goor, Colo Springs; Tammy C. Luttrell, Elbert, both of Colo.

[73] Assignee: Motus, Inc., Colorado Springs, Colo.

[21] Appl. No.: 507,212

[22] Filed: Apr. 9, 1990

Related U.S. Application Data

[63] Continuation-in-part of Ser. No. 495,044, Mar. 16, 1990.

[51] Int. Cl.⁵ .............................................. A61H 1/02
[52] U.S. Cl. .................................. 128/26; 128/25 R; 128/51; 602/16
[58] Field of Search ............... 128/25 R, 26, 88, 80 F, 128/80 C, 25 B, 51-53; 901/21, 38; 623/24, 25, 64

[56] References Cited

U.S. PATENT DOCUMENTS

| | | | |
|---|---|---|---|
| 2,573,866 | 11/1951 | Murphy | 128/80 F |
| 3,976,057 | 8/1976 | Barclay | 128/25 R |
| 4,246,661 | 1/1981 | Pinson | 623/25 |
| 4,566,440 | 1/1986 | Berner et al. | 128/25 R |
| 4,573,455 | 3/1986 | Hoy | 128/80 C |
| 4,716,889 | 1/1988 | Saringer | 128/26 X |
| 4,718,665 | 1/1988 | Airy et al. | 272/132 |

FOREIGN PATENT DOCUMENTS 0961692 10/1982 U.S.S.R. ................. 128/26

Primary Examiner—Richard J. Apley
Assistant Examiner—J. Doyle
Attorney, Agent, or Firm—Beaton & Swanson

[57] ABSTRACT

A dynamic splint which braces any joint and particularly any body joint, and which is capable of cyclically moving the joint through a programmable range of motion while accommodating normal joint component motion and triplanar motion. In a preferred embodiment, a set of inner joint segments nest within a set of outer joint segments and are pivotally attached thereto. An extendable cable slidably attached to the outer joint segments causes a pivoting of the outer joint segments with respect to the inner joint segments and a consequent flexing and extending of the joint.

11 Claims, 2 Drawing Sheets

SEGMENTED DYNAMIC SPLINT

This is a continuation-in-part of application Ser. No. 495,044, filed Mar. 16, 1990, still pending.

BACKGROUND OF THE INVENTION

A loss of joint flexibility is experienced by individuals recovering from neuromuscular diseases, traumatic injuries such as bone fractures, tendon and ligament tears, joint replacements and burns. In order to regain joint flexibility, it is necessary to flex or extend the joint in a repeated, controlled and quantifiable manner. It is also sometimes necessary to apply a relatively small force of a long duration or repeatedly.

Devices have been developed for either flexing or extending joints. Examples of these devices are in U.S. Pat. Nos. 4,508,111, 4,397,308, 4,485,808 and 4,538,600, all by Hepburn. These devices generally comprise upper and lower struts which attach to the limbs of the desired joint using an appropriate attachment means such as velcro or strapping. The upper and lower struts are pivotally attached to one another at the ends adjacent the joint. The pivotal attachment includes a cylindrical housing with a cam, wherein one of the struts is attached to the cam and the other bears on the cam surface through a bearing spring. Flexing or extending the joint causes a corresponding approximation or alignment of the struts relative to one another and a compression or expansion of the spring. The use of the spring allows a somewhat quantifiable and adjustable constant force to be applied to urge the flexing or extending of the joint.

The devices described in the patents named above are a great advance in that they apply a flexing or extending force on the joint rather than simply immobilizing the joint, but they have several drawbacks. One is that they do not provide for cycled flexing and extending. Recently, it has been found that cycled motion is more therapeutic than static force for treating total joint replacements and in many other therapies. Another drawback is that they pivot at a single fixed axis and move through a single plane. In contrast, the normal motion of most body joints includes pivoting at an axis that slides in relation to the joint to produce a "component motion" and that moves through at least three planes in a "triplanar motion." For example, the human knee joint does not pivot at a single axis. Instead, it pivots at an axis that slides down the kneecap, so that the lower leg actually moves away from the upper leg as the knee bends. A similar situation exists in the elbow, ankle and many other joints. The failure to accommodate this movement causes a binding of the pivot mechanism of the device and destructive pressure on the internal body joint-bearing surfaces. Accommodating this movement is particularly difficult because, not only is it complex, it also varies greatly from patient to patient.

Other devices exist which do accommodate component motion to allow normal joint response, but these devices are merely braces to limit the range of joint motion. An example of such a device is in U.S. Pat. No. 4,489,718 by Martin. This device may support the knee joint effectively and allow for limited knee motion, but it does not apply any flexing or extending force to rehabilitate the knee and increase flexibility.

SUMMARY OF THE INVENTION

The present invention is a dynamic splint which supports and manipulates a joint. The configuration is such that a manipulation of the joint can be accomplished in all the natural joint bending and pivot points by application of a single manipulation force at the joint extremities, without any movement between the assembly and the joint and without the need to adjust the configuration for different joint sizes.

In particular, the present invention can be used to support a finger or other body joint while allowing flexing and extending through the normal joint motion including component motion and triplanar motion. It may also apply a controlled and measured force to flex and extend the joint, and may do so in a predetermined cyclical manner. The force-applying mechanism is adjustable to apply a quantified force through a predetermined range of motion and at a predetermined cycle frequency. In this way, joint extension or flexing forces are applied in a single plane while allowing joint movement in all planes. This allows the dynamic splint to produce joint movement in the path of least resistance, rather than forcing joint movement along a predetermined artificial path that may be non-therapeutic or even harmful.

These principles can be accomplished in a number of ways. In a preferred embodiment of the invention, the apparatus includes a set of outer joint manipulation segments pivotally connected to a set of inner joint manipulation segments through pivots in the bottom of the sides of the joint manipulation segments. A flexible cable threaded on one end is threaded through a threaded bracket attached to the upper surface of the distal-most outer joint manipulation segment. The proximal end of the cable is attached to drive means which rotate the cable to thread it back and forth through the threaded bracket to cause an expansion and contraction of the apparatus by pivoting of the outer joint manipulation segments relative to the inner joint manipulation segments. The joint manipulation segment assembly is attached to two extremities of a joint so that this pivoting of the outer joint manipulation segments relative to the inner joint manipulation segments causes flexing and extending of the treated joint along the path of least resistance.

DESCRIPTION OF THE PREFERRED EMBODIMENT

Figure 1:
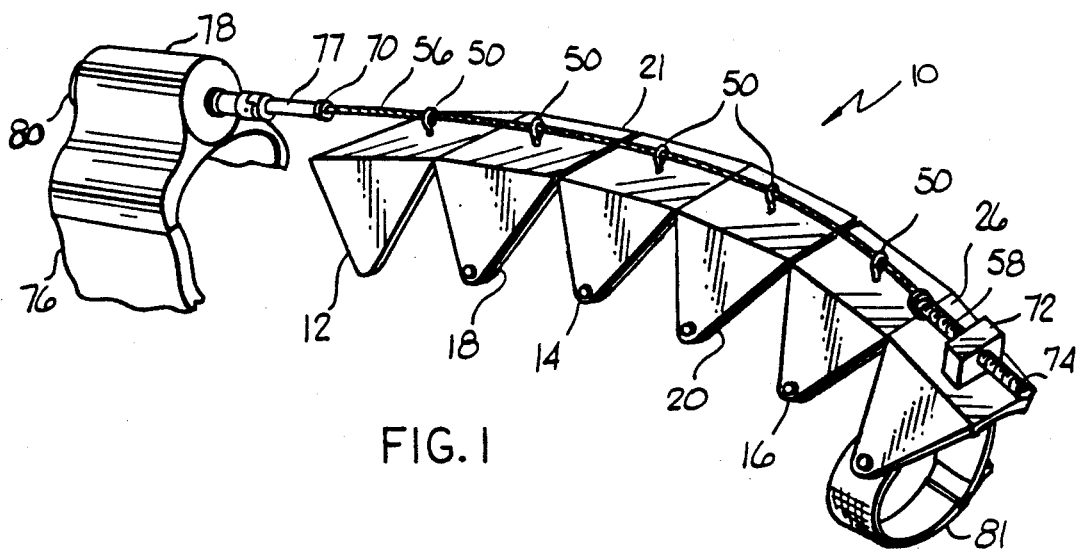
FIG. 1 shows a perspective view of a preferred embodiment of the present invention.

FIG. 1 shows an overall view of the preferred embodiment of the invention 10. A set of outer joint manipulation segments 12, 14 and 16 are pivotally connected to a set of inner joint manipulation segments 18 and 20 to form a joint manipulation segment assembly 21. In the example shown in FIG. 1, there are three outer joint manipulation segments and two inner joint segments in the joint manipulation segment assembly 21, but the invention can utilize any number of segments depending on the type of flexing and extension desired for the joint. A larger number of segments will produce a smoother flexing curve for the joint, while a smaller number of segments will produce a more abrupt flexing curve for the joint.

Figure 2:
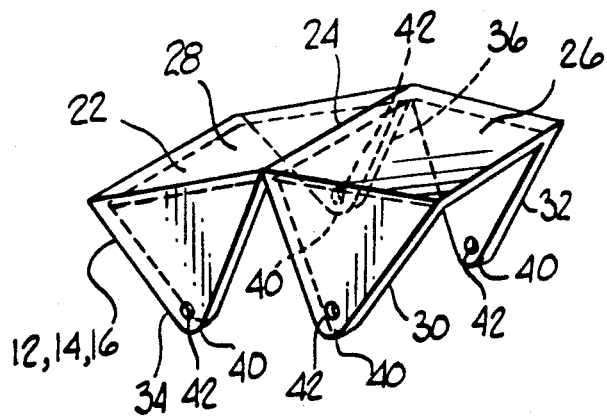
FIG. 2 shows a single outer joint manipulation segment of the invention in perspective.

Referring to FIG. 2, the outer joint manipulation segments 12, 14 and 16 are preferably with an upper surface 22 that has a slight bend 24 to divide the upper surface 22 into a forward portion 26 and an end portion 28. The purpose of the bend 24 will be apparent as the operation of the joint assembly 21 is described below. Each of the forward portion 26 and end portion 28 has a depending flange on each side. In FIG. 2, the flange on the near side of the forward portion 26 is flange 30, the flange on the far side of the forward portion 26 is flange 32, the flange on the near side of the end portion 28 is flange 34, and the flange on the far side of the end portion 28 is flange 36. Each flange 30, 32, 34 and 36 is triangular shaped and lies in a plane roughly perpendicular to the upper surface forward portion 26 or end portion 28 to which it is attached. The lower point 40 of each flange 30, 32, 34 and 36 has a hole 42.

Figure 3:
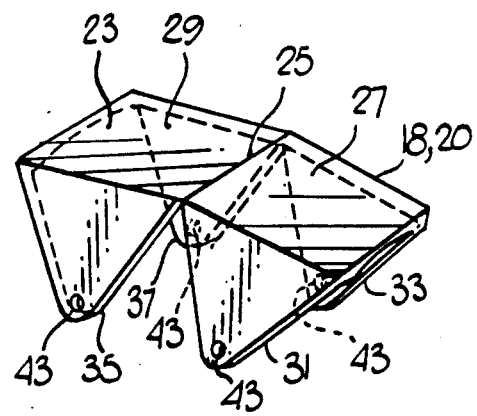
FIG. 3 shows a single inner joint manipulation segment of the invention in perspective.

The inner joint manipulation segments 18 and 20 and outer joint segments 12, 14 and 16 all have the same general configuration as the outer joint manipulation segments (12, 14 and 16). As shown in FIG. 3, as in the case of the outer joint manipulation segments 12, 14 and 16, the inner joint manipulation segments 18 and 20 have an upper surface 23 which has a slight bend 25 to divide the surface into a forward portion 27 and end portion 29, a set of flanges 31, 33, 35 and 37, and a hole 43 in each flange. However, as shown in FIG. 3, the distance between the flanges 31 and 33 of the forward portion 27 and the flanges 35 and 37 of the end portion 29 of the inner joint manipulation segments 18 and 20, is less than the distance between the flanges 30 and 32 of the forward portion 26 and the flanges 34 and 36 of the end portion 28 of the outer joint manipulation segments 12, 14 and 16. This smaller width allows the inner joint manipulation segments 18 and 20 to nest in the outer joint manipulation segments 12, 14 and 16 in the manner described below.

Figure 4:
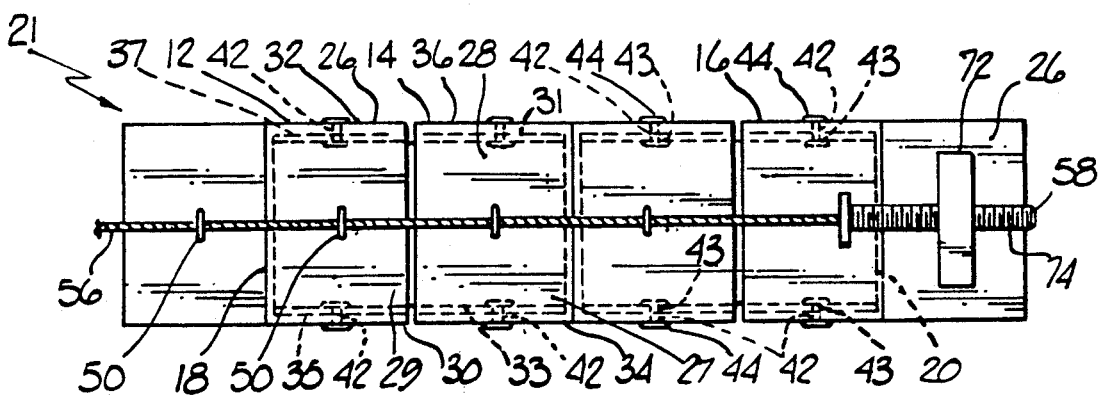
FIG. 4 is a top plan view of the joint manipulation segments of the invention.

FIG. 4 shows the nesting of the inner joint manipulation segments 18 and 20 into the outer joint manipulation segments 12, 14 and 16. The end portion 29 and its two flanges 35 and 37 of each inner joint manipulation segment 18 and 20 nest into the forward portion 26 and its two flanges 30 and 32 of the outer joint manipulation segments 12 and 14 (but excluding the distal-most outer joint manipulation segment 16). Similarly, the forward portion 27 and its two flanges 31 and 33 of each inner joint manipulation segment 18 and 20 nest into the end portion 28 and its two flanges 34 and 36 of the outer joint manipulation segments 14 and 16 (but excluding the proximal-most outer joint manipulation segment 12).

The inner joint manipulation segments 18 and 20 are pivotally attached to the outer joint manipulation segments 12, 14 and 16 as shown in FIG. 4. The holes 42 of each outer joint manipulation segment are aligned with the holes 43 of each nesting inner joint manipulation segment. For example, the holes 42 in the forward portion 26 flanges 30 and 32 of the proximal-most outer joint manipulation segment 12 are aligned with the holes 42 in the end portion 29 flanges 35 and 37 of the proximal-most inner joint manipulation segment 16. The aligned holes receive a pin 44 or other pivotal retaining means to allow pivoting of the outer joint manipulation segment 12 with respect to the inner joint manipulation segment 18 about the pin 44.

The upper surface of each of the forward portion 26 and end portion 28 of each outer joint manipulation segment 12, 14 and 18 has an eyelet 50. The eyelets slidably receive a flexible cable 56. On the forward portion 26 of the distal-most outer joint manipulation segment 16, the eyelet 50 is replaced with a threaded bracket 72. The distal end 58 of the cable 56 has mating threads 74 which are threaded through the threaded bracket 72. The termination of the cable 56 proximal end 70 is attached to a spring 77 which is both expandable and contractible. The other end of the spring 77 is attached to a rotation drive means such as a motor 78. The motor may contain programmable control means 80. The motor 78 and programmable control means 80 may be attached to the patient with a cuff 76 which is releasably attached to the patient in the area of the joint using velcro straps or other appropriate attaching means (not shown). The joint manipulation segment assembly 21 is attached to the joint also using velcro or other suitable attachment means, shown as 81 in FIG. 1.

The apparatus operates as follows. The control means 80 directs the drive means 78 to turn clockwise or counterclockwise for predetermined speeds, for predetermined cycles per time period, and for a predetermined total time or total number of cycles. The turning of the drive means causes a proportionate turning of the flexible cable 56 and consequently threads the cable 56 threads 72 through the threaded bracket 72. This causes a lengthening or shortening of the cable 56 portion between the cuff 76 and the threaded bracket 72.

Figure 5:
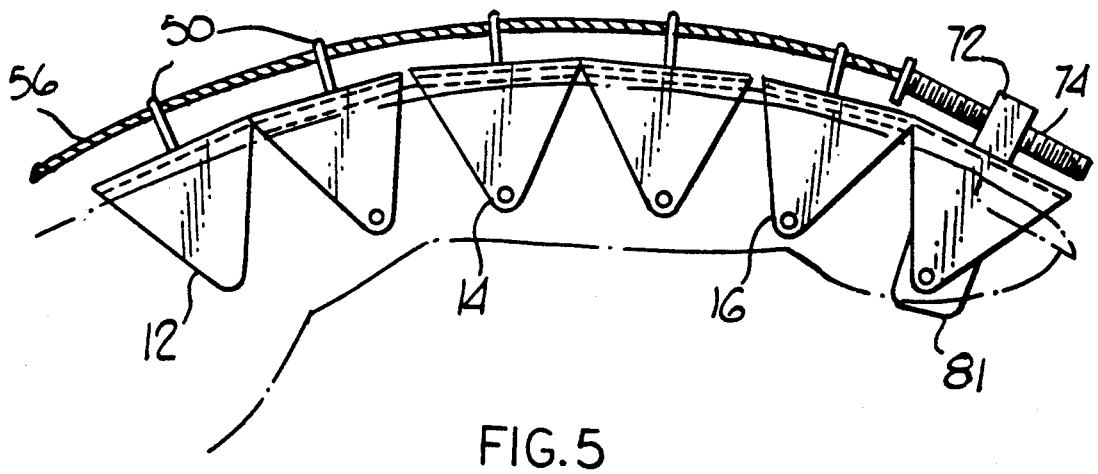
FIG. 5 is an elevational view, taken along line 4—4 of FIG. 3.
Figure 6:
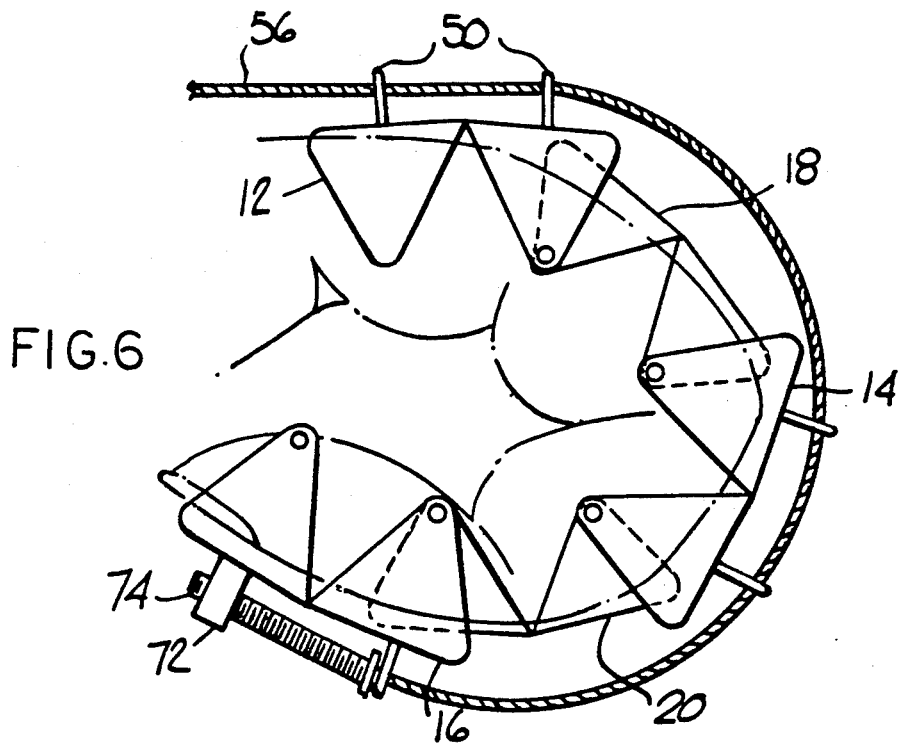
FIG. 6 is an elevational view of a portion of the invention, showing the expansion of the apparatus by the pivoting of the outer joint manipulation segments with respect to the inner joint manipulation segments.

Because the imaginary arc formed by the pins 44 is smaller than and is concentric with the arc formed by the flexible cable 56, this effective lengthening of the cable 56 urges a pivoting of the outer joint manipulation segments 12, 14 and 16 with respect to the inner joint manipulation segments 18 and 20 about the pins 44. The outcome of this pivoting is a bending of the joint as shown in FIG. 5. The bending is limited by the strength of the spring 77.

An important advantage to this operation of the apparatus is that the flexing and extending of the joint occurs in the normal joint flexing and extending points, rather than at predetermined artificial points Further, when the apparatus is attached to several joints, as in a finger, it allows the several joints to be manipulated naturally relative to one another, rather than in a predetermined degree. For example, flexing a finger 90 degrees may be accomplished by flexing the first joint 70 degrees and flexing the second joint 20 degrees, or in any other combination depending on the natural flexibility of the two joints. Of course, if a predetermined flexing amount is desired, that can also be accomplished by fixing the pivot pins adjacent the joints that are not to flex.

A further important advantage of this operation is that the configuration allows the joint to be flexed and extended without the need for movement of the apparatus relative to this joint. Ordinary joint flexing and extending causes a lengthening and shortening of the joint surface since the actual flexing and extending occurs within the joint. In other devices, this produces a chafing between the device and the joint surface, since the device itself is a constant length at the surface contact with the joint. In the present apparatus, however, the apparatus length becomes longer and shorter as the joint flexes or extends, thereby maintaining constant joint surface contact without any chafing.

Figure 7:
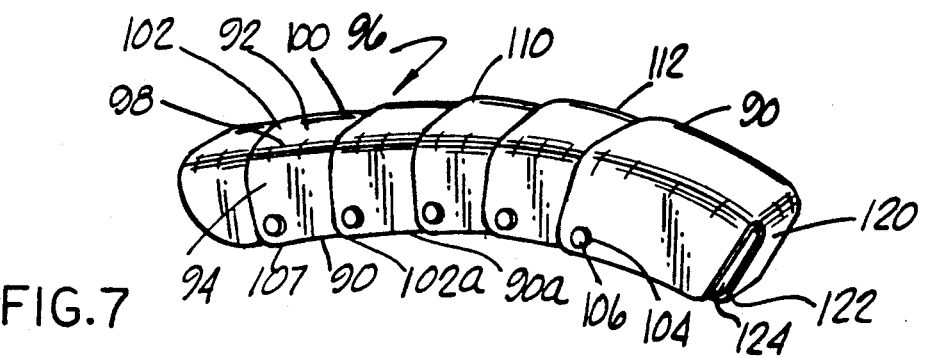
FIG. 7 is a perspective view of a portion of an alternate embodiment of the invention.

An alternate embodiment of the invention is shown in FIG. 7. In the alternate embodiment, each of the joint manipulation segments 90 has the same configuration, rather than the outer joint manipulation segments having a configuration different than the inner joint manipulation segments. Each manipulation segment 90 is channel-shaped with an upper portion 92 and a depending flange 94 and 96 on each side. The depending flanges 94 and 96 are attached to the top portion 92, preferably by being joined integrally therewith through a smoothly curved joining portion 98. This construction allows the manipulation segment 90 to be stamped from a single sheet of material such as metal or plastic and then formed into the desired channel shape.

Each manipulation segment 90 has a forward end 100 and an anterior end 102. The forward end 100 is narrower than the anterior end 102, so that the forward end 100 of each manipulation segment 90 nests into the anterior end 102 of the adjacent manipulation segment. For example, in FIG. 7, the forward end 100 of manipulation segment 90 nests into the anterior end 102A of the adjacent manipulation segment 90A.

As in the preferred embodiment, the alternate embodiment utilizes a set of pivot holes 104 and pivot pins 106. Each manipulation segment 90 has a forward pivot hole and pivot pin and a rear pivot hole and pivot pin in each flange 94 and 96. The pivot holes and pivot pins are located toward the bottom 107 of each flange 94 and 96, so that a pivoting of one manipulation segment with respect to another causes an effective lengthening of the top portion of the assembled manipulation segment. This allows the pivoting to be driven by the extendable cable system (not shown) described in connection with the preferred embodiment.

Unlike the first embodiment, however, the joint manipulation segments 90 utilized in this alternate embodiment gradually narrow from one end to the other so that there is a wide end 110 and a narrow end 112. The narrow end 112 of each manipulation segment nests within the wide end 110 of the adjacent manipulation segment. In this way, the joint manipulation segments 90 telescope together. Because most of them are the same, manufacturing costs are reduced.

The forward-most manipulation segment 90 has a forward end 120 with a forward depending flange 122 which folds over and underneath the top of a finger. The fingertip therefore fits into the cavity 124 formed by this forward depending flange and the two side depending flanges 94 and 96, to allow the assembly to be secured to the fingertip without strapping on other separate attachment means.

The pivot pins 106 may be releasable so that an unlimited number of additional manipulation segments 90 can be releasable attached to the proximal end of the assembly. This allows the assembly to be lengthened to accommodate larger joints.

While the invention has been described with the configuration set forth above, other configurations to achieve the same or similar results are possible. For example, the joint manipulation segments could have a continuously curved upper surface rather than two discrete portions. The joint manipulation segments could have flanges with a variety of shapes rather than triangular shapes, and the flanges could be continuous on each side of the joint manipulation segment rather than two discrete portions, so long as the outer joint manipulation segments may pivot with respect to the inner joint manipulation segments. Rather than the flanges of each manipulation segment alternating against the joint surface as shown in the drawings, all the forward flanges or all the rearward flanges could be against the joint surface to produce a telescoping effect.

What is claimed is:

1. An apparatus for manipulating a joint including a body joint, comprising;
   a plurality of joint manipulation segments adjacent to each other from a proximal end to a distal end on a joint, each said segment having a forward portion toward the distal end and an end portion toward the proximal end, the forward portion of each said segment being pivotally attached to the end portion of the distally adjacent segment, and an interior surface in contact with the joint, said interior surface at least partially surrounding said joint;
   means to attach at least one of said plurality of manipulation segments to the joint; and
   means for pivoting said manipulation segments with respect to one another whereby said plurality of manipulation segments urges the joint to flex or extend, the pivoting means including an extendable cable, one end of said extendable cable being threaded through a threaded bracket mounted on one end of said plurality of manipulation segments, and the other end of said extendable cable being mounted to rotation drive means, whereby the rotation of said drive means threads the extendable cable through the threaded bracket to adjust the cable length between the drive means and threaded bracket, thereby urging a pivoting of said manipulation segments with respect to one another to flex or extend the joint.

2. The apparatus of claim 1, wherein each of said manipulation segments has an upper portion on the upper side of the joint, and a first depending flange attached to the upper portion on the side of the joint, and wherein said pivotal attachments are in said first depending flange.

3. The apparatus of claim 2, wherein each of said manipulation segments has a second depending flange attached to the upper portion on the side of the joint opposite said first depending flange, and wherein said pivotal attachments are in each of said first depending flange and second depending flange.

4. 10. The apparatus of claim 3, wherein each of said first depending flange and second depending flange has a forward portion and a rearward portion, and wherein said pivotal attachments are in each of said depending flange forward portions and depending flange rearward portions.

5. The apparatus of claim 4, wherein the depending flanges of each manipulation segment are attached either inside or outside of the depending flanges of the adjacent manipulation segment to which said each manipulation segment is pivotally attached.

6. The apparatus of claim 5, wherein each manipulation segment that has flanges that are attached outside the depending flanges of an adjacent manipulation segment, has depending flanges that are attached outside the depending flanges of any manipulation segment that may be adjacent on the opposite end of said each manipulation segment, and each manipulation segment that has depending flanges that are attached inside the depending flanges of an adjacent manipulation segment, has depending flanges that are attached inside the depending flanges of any manipulation segment that may be adjacent on the opposite end of said each manipulation segment.

7. The apparatus of claim 5, wherein each manipulation segment that has flanges that are attached outside the depending flanges of an adjacent manipulation segment, has depending flanges that are attached inside the depending flanges of any manipulation segment that may be adjacent on the opposite end of said each manipulation segment, and each manipulation segment that has depending flanges that are attached inside the depending flanges of an adjacent manipulation segment, has depending flanges that are attached outside the depending flanges of any manipulation segment that may be adjacent on the opposite end of said each manipulation segment.

8. The apparatus of claim 4, wherein said forward and rearward portions of said depending flanges are substantially triangular shaped and one leg of said triangle is attached to the manipulation segment upper portion and said pivot pins are located in the triangle point opposite the attachment to the manipulation segment upper portion.

9. The apparatus of claim 8, wherein said manipulation segment upper portion has a bend in the longitudinal direction of the joint, and wherein said bend limits the degree of joint extension.

10. An apparatus for manipulating a joint including a body joint, comprising:

a plurality of joint manipulation segments adjacent to each other from a proximal end to a distal end on a joint, each said segment having a forward portion toward the distal end and an end portion toward the proximal end, the forward portion of each said segment being pivotally attached to the end portion of the distally adjacent segment;

means to attach at least one of said plurality of manipulation segments to the joint; and means for pivoting said manipulation segments with respect to one another whereby said plurality of manipulation segments urges the joint to flex or extend, wherein said pivoting means includes an extendable cable, one end of said extendable cable being threaded through a threaded bracket mounted on one end of said plurality of manipulation segments, and the other end of said extendable being mounted to rotation drive means, whereby the rotation of said drive means threads the extendable cable through the threaded bracket to adjust the cable length between the drive means and threaded bracket, thereby urging a pivoting of said manipulation segments with respect to one another to flex or extend the joint; and a spring disposed between said drive means and said cable to limit the amount of flexing and extending force applied to the joint.

11. The apparatus of claim 10, further comprising a plurality of eyelets mounted to the upper surface of said manipulation segments and wherein said cable is slidably mounted in said eyelets.

* * * * *